(12) United States Patent  
Hafner

(10) Patent No.: US 7,972,331 B2  
(45) Date of Patent: Jul. 5, 2011

(54) ELECTROSURGICAL INSTRUMENT WITH OPPOSING JAWS, CENTRAL KNIFE, AND BARBS FOR MAINTAINING CLAMPING TENSION ON TISSUE EVEN AFTER OPENING JAWS

(75) Inventor: Dieter Hafner, Tubingen (DE)

(73) Assignee: ERBE Elecktromedizin GmbH, Tübingen (DE)

( * ) Notice: Subject to any disclaimer, the term of this patent is extended or adjusted under 35 U.S.C. 154(b) by 721 days.

(21) Appl. No.: 11/573,305

(22) PCT Filed: Jul. 14, 2005

(86) PCT No.: PCT/EP2005/007681  
§ 371 (c)(1),  
(2), (4) Date: Feb. 6, 2007

(87) PCT Pub. No.: WO2006/018083  
PCT Pub. Date: Feb. 23, 2006

(65) Prior Publication Data  
US 2007/0185487 A1    Aug. 9, 2007

(30) Foreign Application Priority Data

Aug. 11, 2004 (DE) .......................... 10 2004 039 051  
Nov. 18, 2004 (DE) .......................... 10 2004 055 670

(51) Int. Cl.  
*A61B 18/14* (2006.01)

(52) U.S. Cl. .............................. 606/45; 606/51; 606/171

(58) Field of Classification Search .............. 606/48–52, 606/171; 607/101  
See application file for complete search history.

(56) References Cited

U.S. PATENT DOCUMENTS

| 5,443,463 | A | 8/1995 | Stern et al. |
| 5,458,598 | A | 10/1995 | Feinberg et al. |
| 6,267,761 | B1 | 7/2001 | Ryan |
| 6,273,887 | B1 | 8/2001 | Yamauchi et al. |
| 6,775,575 | B2 * | 8/2004 | Bommannan et al. ........ 607/101 |
| 2001/0037109 | A1 | 11/2001 | Yamauchi et al. |
| 2003/0130677 | A1 | 7/2003 | Whitman et al. |
| 2003/0171747 | A1 * | 9/2003 | Kanehira et al. ................ 606/45 |
| 2003/0181910 | A1 * | 9/2003 | Dycus et al. .................... 606/51 |
| 2004/0049185 | A1 | 3/2004 | Latterell et al. |

FOREIGN PATENT DOCUMENTS

WO    9717033    5/1997

* cited by examiner

*Primary Examiner* — Michael Peffley  
*Assistant Examiner* — Benjamin Lee  
(74) *Attorney, Agent, or Firm* — Dickstein Shapiro LLP

(57) ABSTRACT

The invention concerns an electrosurgical instrument comprising two articulated limbs, which can be actuated in the manner of a cutting or a clamping tool. The instrument further comprises opposing electrode parts with coagulating surfaces at the distal ends of the limbs for grasping a vessel or tissue and for conducting a coagulating current through the vessel or tissue in order to cause it to coagulate, as well as current-supplying devices for supplying the coagulating current to the electrode parts from a HF generator. In addition, the electrode parts each have at least one clamping region, such that clamped tissue is pretensioned between the electrode parts in order that a cutting procedure can be carried out on the pretensioned tissue by means of a cutting instrument.

16 Claims, 3 Drawing Sheets

ELECTROSURGICAL INSTRUMENT WITH OPPOSING JAWS, CENTRAL KNIFE, AND BARBS FOR MAINTAINING CLAMPING TENSION ON TISSUE EVEN AFTER OPENING JAWS

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The invention concerns an electrosurgical instrument comprising two limbs that have an articulated connection and that can be actuated in the manner of a cutting or clamping tool.

BACKGROUND OF THE INVENTION

Electrosurgical instruments have been used for many years in high-frequency surgery, in particular to coagulate biological tissue, as well as to cut it. With coagulation, a high-frequency current is passed through the tissue being treated, causing it to alter due to protein coagulation and dehydration. The tissue contracts in such a way that the vessels occlude and bleeding is staunched. Once coagulation has occurred, the tissue can be cut through, for example, by means of a mechanically operating cutting instrument.

Electrosurgical procedures can be carried out in both a monopolar and a bipolar manner. With the monopolar technique the electrosurgical instrument has only a single current supply; accordingly, the tissue (or a patient) to be treated must be placed on the other potential. However, bipolar instruments which are configured with two sections electrically insulated from each other are increasingly gaining in importance. The current path between the electrode parts can thus be calculated and does not proceed any distance through the body of the patient. Thus the effect of, for example, pacemakers or other appliances which are connected to the patient during the operation is reduced.

Bipolar coagulating instruments have essentially two articulated limbs, at the proximal ends of which gripping devices are provided for handling the limbs. At the distal ends of the limbs, there are electrode parts for grasping tissue and for conducting the coagulating current through the tissue. Also, the HF current supplied by a HF generator is conducted via current-supplying devices to the electrode parts of the bipolar instrument.

Once coagulation has occurred, the cutting procedure is generally carried out by means of a cutting instrument. With mechanical cutting, the surgeon must exert force in order to carry out the cut, which, on the one hand, produces a mechanical strain on the cutting instrument and, on the other, promotes abrasive wear of the cutting sections. Also, as a result of such wear, particles of the cutting sections will remain in the tissue, causing an increased risk of infection.

A reduction in the expendable cutting force is effected with conventional cutting instruments, for example, by means of transmission mechanisms that are elaborate to manufacture and expensive. At the same time, the instruments are frequently constructed to be extremely stable, to counteract the mechanical strain. Instruments of a large constructed size, however, are precisely unsuited to endoscopic procedures.

Other solutions provide for the cutting sections to be coated, to reduce the abrasive wear. This requires an elaborate and expensive process. In addition, the coated sections can only be inadequately reworked, that is to say, for example, reground. To avoid reworking, the instruments, in particular the cutting sections, are often constructed as disposable or semi-reusable instruments, incurring high costs here, too.

BRIEF SUMMARY OF THE INVENTION

It is an object of the invention to provide an electrosurgical instrument wherein, with respect to conventional instruments, the force applied to cut a vessel or a tissue by means of a cutting instrument is reduced and, any mechanical strain on the cutting instrument, in particular any wear of cutting sections, is also reduced.

According to the invention an electrosurgical instrument comprises two articulated limbs which can be actuated in the manner of a cutting a clamping tool. In addition, the instrument includes opposing electrode parts with coagulating surfaces at distal ends of the limbs for grasping a vessel or tissue and for conducting a coagulating current through the vessel or tissue in order to cause it to coagulate, as well as current-supplying devices for supplying the coagulating current to the electrode parts from a HF generator. The electrode parts each have at least one clamping region, such that upon clamping the vessel or tissue the latter is pretensioned between the electrode parts and a cutting procedure can be carried out on the pretensioned vessel or tissue by means of a cutting instrument.

The basis of the invention is that as the tissue is pulled, i.e. stretched, by the clamping regions of the coagulating instrument on both sides in the direction of their end areas, this makes the tensioned tissue easier to cut by means of the mechanically operating cutting instrument. This is because fibres of the tissue are aligned crossways to the cutting direction and the tissue here becomes thinner. As a result, any force applied the pretensioned tissue to cut it through completely is considerably reduced, and any mechanical strain on the cutting instrument, in particular any wear of cutting sections, is counteracted. It is also easier for the surgeon to realise the cutting procedure, and the instrument is easier to handle.

In a first preferred embodiment, one of the clamping regions is curved in a convex manner at least in a first central section, while the clamping region opposing it is curved in a concave manner at least in a second central section. As a result, the clamping regions essentially fit positively into each other when the limbs are brought together. The curved clamping regions enable the tissue to be clamped in the simplest manner, because the latter is stretched over the clamping regions. Owing to the positive fit, the tissue is safely arrested between the limbs in a clamped state.

The terms "convex" and "concave" are not merely to be understood in this context as a rounded arc. Rather, these terms both here and in the claims are intended to cover not only a surface which defines a rounded arc but also any type of elevation or recess, that is to say, for example, apse a roof-shaped elevation and, correspondingly, a V-shaped recess.

In a further preferred embodiment, one of the clamping regions is curved in a convex manner at least in the first central section, while the clamping region opposing it is curved in a concave manner at least in the second central section. Here, a radius of curvature of the concavely curved clamping region is larger at least in the second central section than a radius of curvature of the convexly curved clamping region in the first central section. The curvatures run around longitudinal axes of the distal ends in such a way that the tissue held between the distal ends and running perpendicular to the longitudinal axes is held with increasing compression relative to the first and second central section. This embodiment has the advantage that the tissue is arrested particularly securely between the clamping regions due to the increasing compression. Any sliding of the tissue once grasped is thus ruled out. In addition, safe closure of the tissue is achieved at the areas of high compression, i.e. high pressure, due to the strong clamping force.

One solution according to the invention provides for at least one clamping region having at least one passage for the cutting instrument, with the result that at least one section of the passage is provided as a guide opening for the cutting instrument and the cutting instrument may be applied to the clamped tissue to carry out the cutting procedure. The guide opening enables a precise cut of the tissue to be made, in particular with mechanical cutting tools.

Preferably, the passage divides the respective electrode parts into at least two areas, with the result that the electrode parts each have opposing split surfaces arranged parallel to each other. As a result, the passage can be used as a guide opening over its entire area. This type of guide opening enables an extremely precise cut to be made because the cutting instrument, in particular the mechanically operated kind, can be guided in a particularly precise manner.

A further preferred embodiment provides for the passage dividing the respective electrode parts into at least two areas, with the result that the electrode parts each have opposing split surfaces arranged in a tapering manner relative to each other in the direction of the coagulating surfaces. Since the split surfaces of the corresponding electrode parts converge on one cutting area on the tissue, this further guarantees precise guidance of the cutting instrument here. The part of the passage spread apart and directed away from the cutting area is particularly suited to reprocessing, that is to a cleaning of the instrument after a successful intervention or also to the subsequent application of a coating of the split surfaces with, for example, a wear-resistant ceramic, since improved accessibility is guaranteed due to the physical form of the passage.

Preferably, the passages are provided on the opposing clamping ranges, in which case these essentially adjoin each other in alignment when the limbs are brought together. If only one passage is configured on an electrode part, this is particularly suited to cutting through the tissue, for example, by means of surgical knife, in which case the tissue lies, in a clamped state, completely on the opposing electrode part. If passages are provided on both electrode parts, surgical scissors, for example, may be applied to the coagulated tissue and this may be cut through in a simple manner. To achieve a well-calculated cut, the passages are preferably arranged in the central sections of the clamping regions.

In one preferred embodiment, the cutting instrument is configured connected to the electrosurgical instrument. For example, the cutting instrument is located within one of the limbs and can be brought into a cutting position if so required. Thus a change of instrument can be avoided, with the result that the course of an operation need not be interrupted.

With the cutting instrument integrated into the coagulating instrument, both electrode parts are preferably configured with the passage, so that the cutting instrument can reach the tissue unhindered.

If the cutting instrument is not integrated in the electrosurgical instrument, the guide opening should be constructed in such a way that an externally entering cutting instrument can be applied to the pretensioned tissue with sufficiently accurate guidance.

One advantageous embodiment provides for the cutting instrument being mechanically and/or electrically actuated. Thus, for example, a blade configured on a shaft may be provided on the electrosurgical instrument, which blade is accommodated during coagulation in the limb and introduced to the tissue for the cutting procedure. The positioning of the blade or of another cutting instrument and also any advance motion may occur here in a self-acting manner or also be carried out mechanically by the surgeon.

One solution according to the invention provides for a surface profile which supports a clamping effect being configured on the one clamping region and/or on the opposing clamping region. The profile is preferably configured at end areas of the respective clamping region and additionally moves the tissue in a direction of traction defined by the clamping regions or prevents any retreating of the tissue against this direction of traction.

Preferably, the surface profile supporting a clamping effect is configured as a saw-tooth profile. Teeth of the profile may be arranged in such a way, for example, that they reach further and further into the tissue when the limbs are brought together and take this along in the direction of traction. As a result, the tension in the tissue is significantly increased. It is important, however, that damage to the tissue is avoided by the profile, and to this end the teeth are preferably configured as rounded nodules.

Preferably, the profile is formed in such a way that the tissue is held by the profile in its clamped position when the limbs are slightly opened. The profile accordingly functions as an arrangement of barbs.

In one preferred embodiment, the surface profile supporting the clamping effect is configured in such a way that at least one constriction is provided between the electrode parts. This is particularly useful with electrode parts that have equal radii of curvature. That is to say, the coagulating surfaces of the electrode parts are preferably formed at the two end areas in such a way that the tissue is taken along in the direction of the end areas when the limbs are brought together and, in each case when the limbs are brought together, is clamped in a constriction relative to the rest of the area. The constriction also has the advantage that the coagulating surfaces are able to be configured essentially smooth and are thus easy to clean. In addition, damage to the tissue is prevented due to the smooth surface.

In one advantageous embodiment, an insulating section is configured on at least one of the coagulating surfaces, allowing direct electrical contact between the coagulating surfaces to be avoided. Because of heat-conducting properties of the insulating section, coagulation of the tissue is guaranteed on the latter too. The insulating section is provided, depending on the physical form of the electrode parts, on the areas of at least one coagulating surface which are closest to the opposing coagulating surface. This is particularly necessary when the clamping regions and thus the coagulating surfaces have a different radius of curvature. Preferably, the insulating section is then arranged at the central area of the clamping region or clamping regions and thus prevents a short circuit between the electrode parts. At the same time, the clamping effect is further promoted by the insulating section.

If the insulating section is configured on the areas of at least one coagulating surface in closest proximity to the opposing coagulating surface, it may close flush with the respective coagulating surface. The surface portion of the coagulating surface that describes the area in closest proximity to the opposing coagulating surface must then, however, be configured completely from insulating material, with the result that contact between the conductive areas of the coagulating surfaces is avoided. With the convexly or concavely configured, opposing clamping regions or coagulating surfaces with different radii of curvature, the insulating section should be arranged along a crown line of at least one coagulating surface. Advantageously, the insulating section in this embodiment is accommodated in a protected manner in the respective electrode part and thus safe from wear.

Alternatively, it is possible to configure the insulating section in such a way that this protrudes from the respective coagulating surface. In this case, the insulating section does not only serve to isolate but also to bend repeatedly the tissue being treated and so achieve improved arresting of the tissue between the distal ends of the electrosurgical instrument.

In one preferred embodiment, the insulating section, i.e. the insulating section protruding from the respective coagulating surface, is configured from several segments. This enables particularly secure arresting of the tissue between the electrode parts, because the tissue is repeatedly bent at edges of the insulating section.

One solution according to the invention provides for the insulating section itself being configured in a structured manner, to achieve optimum arresting of the tissue.

One preferred embodiment provides for the insulating section being configured from ceramic or diamond. Advantageously, ceramic and diamond have among other things a high degree of resistance to corrosion and a high degree of resistance to wear from mechanical strain.

In a further preferred embodiment, the insulating section is configured as the particular or any surface profile supporting the particular or any clamping effect. As a result, both the short circuit between the electrode parts is avoided and the tensioning of the tissue is reinforced in the simplest way.

A device preventing a short circuit between the electrode parts may also be provided on the limbs, for example. If a spacer, for example, is arranged on the latter, the limbs cannot be brought together completely, leaving a clearance between the electrode parts.

Electrosurgical instruments of this type may, for example, be configured for use on the opened body. The principle of the electrode parts configured with a clamping region is, however, also applicable to instruments used in endoscopy. The electrode parts attached to the limbs and, if so required, the cutting instrument are then actuated via a hand grip attached to a shaft, for example, or a control unit may be provided, allowing actuation of the electrode parts and/or the cutting instrument to be controlled by this means. Thus the electrosurgical instrument is preferably configured as a laparoscopic instrument.

Embodiment of the invention will now be described by way of example with reference to the accompanying drawings.

DETAILED DESCRIPTION OF THE INVENTION

Figure 1:
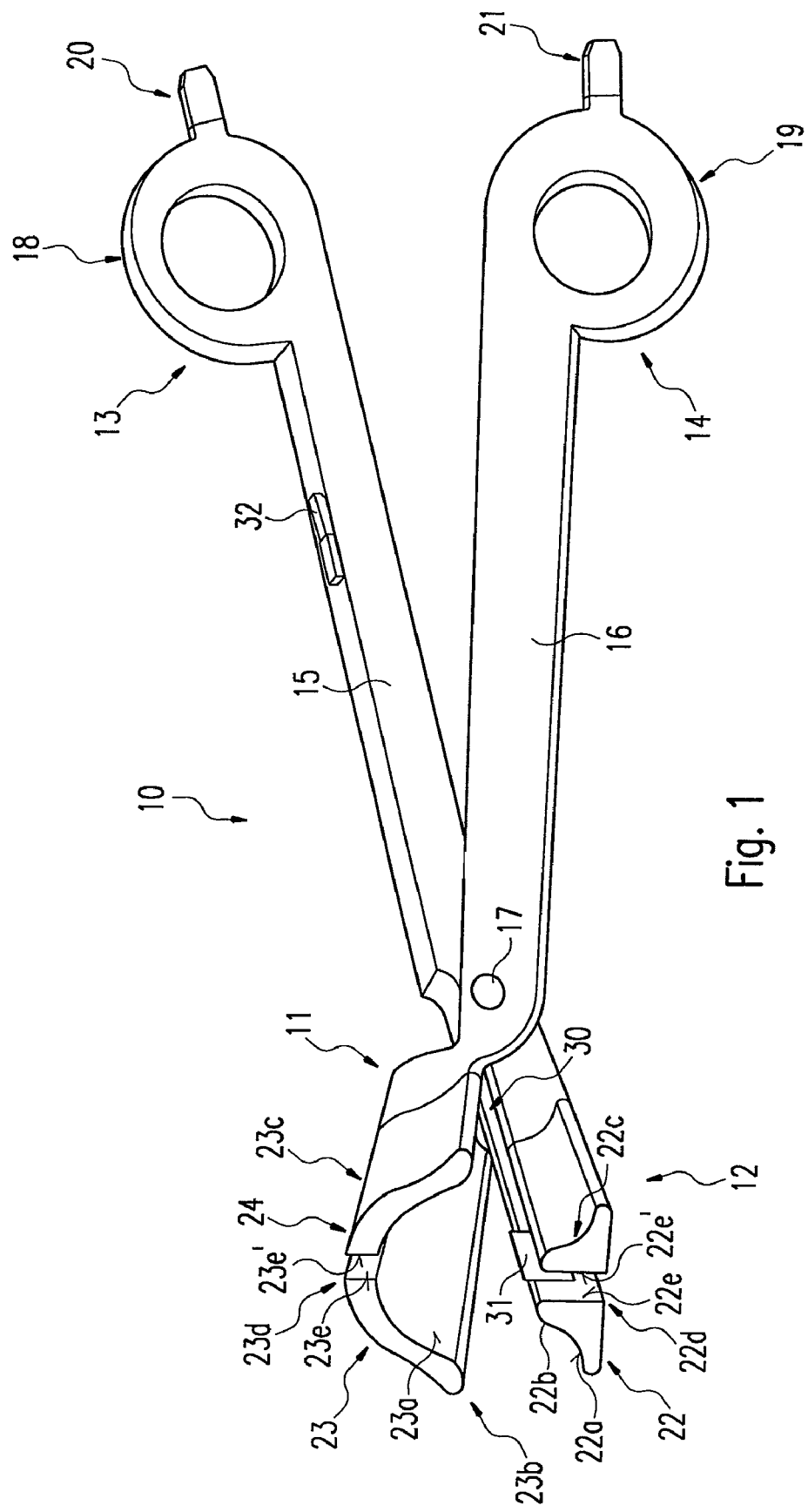
FIG. 1 is a perspective view of a first embodiment of electrosurgical instrument with an electrode arrangement according to the invention.

In the following description, the same reference numerals are used for the same and similarly working parts.

FIG. 1 depicts a perspectively represented electrosurgical instrument 10 with an electrode arrangement according to the invention in a first preferred embodiment. The instrument 10 is configured for intervention on the opened body. In the figure, two limbs of the electrosurgical instrument 10 are identified by the reference numerals 15 and 16. The two limbs 15, 16 are connected to each other via an spindle 17 and can be pivoted around this. They have distal ends 11, 12 provided with electrode parts 22, 23, wherein the electrode parts 22, 23 oppose each other. With the aid of the electrode parts 22, 23, which have coagulating surfaces 22a, 23a, it is possible to grasp a vessel or tissue, for example, and to coagulate or cut this by supplying a high-frequency current. In addition, gripping parts 18, 19 are provided which are attached to respective proximal ends 13, 14 of the limbs 15, 16. The proximal ends 13, 14 of the limbs 15, 16 each end in a current connection element or a current-supplying device 20, 21 to connect the electrosurgical instrument 10 to a HF generator (not represented), which produces a HF voltage, so that a HF current may be supplied to the electrode parts 22, 23 by, for example, electrical leads (not depicted) running through the instrument 10.

The electrosurgical instrument 10 is configured in such a way that one electrode part 23 protrudes over the other electrode part 22 when the limbs 15, 16 are brought together, i.e. cover the latter. As can be seen from the figure, the electrode parts 22, 23 are configured in a curved manner. At the same time, one electrode part 22 has a convex curvature 22b and the electrode part 23 opposing the convex electrode part has a concave curvature 23b. As a result, the electrode parts 22, 23 fit positively into each other when the limbs 15, 16 are brought together. It is through the curved electrode parts 22, 23 that the tissue is pulled, i.e. stretched, in the direction of end areas of the electrode parts 22, 23. The electrode parts 22, 23 accordingly form clamping regions 22c, 23c. As a result, the tissue is easier to cut, because fibres of the tissue are aligned crossways to a cutting direction and the tissue here becomes thinner. Owing to the positive fit, the tissue is fixed between the limbs 15, 16 in a clamped state. In this embodiment example, the electrode parts 22, 23 are essentially configured completely as clamping regions 22c, 23c. Alternatively, it is possible that only sections of the electrode parts form clamping regions.

The clamping regions 22c, 23c have passages 22d, 23d, which form a guide opening 24 for a cutting instrument 30. The cutting instrument 30 can accordingly be applied to the clamped tissue to carry out a cutting procedure. The guide opening 24 enables in addition a precise cut of the tissue to be made because the cutting instrument 30 can be guided along the guide opening 24. This is advantageous when the cutting instrument is mechanically operated. At the same time, the clamping regions 22c, 23c prevent the tissue from entering the guide opening since the tissue is pulled away from and out of the latter due to the tensioning.

Since both clamping regions 22c, 23c have passages 22d, 23d, these are arranged in alignment with each other. Only in this way is precise guidance of the cutting instrument 30 guaranteed.

As depicted in this embodiment example, the passages 22d, 23d divide the respective electrode parts 22, 23 into at least two areas, with the result that the electrode parts 22, 23 each have opposing split surfaces 22e, 22e' and 23e, 23e' arranged parallel to each other. As a result, the passages 22d, 23d can be used over their entire length as a guide opening 24. This type of guide opening 24 enables an extremely precise cut to be made because the cutting instrument 30 can be guided in a particularly precise manner, in particular when the cutting instrument is mechanically operated.

Alternatively, it would be possible to configure only one passage on an electrode part, enabling the tissue to be cut through, for example, by means of a surgical knife. In this case, the tissue lies, in a clamped state, completely on the opposing electrode part.

The cutting instrument 30 has a blade 31 on a shaft and is accommodated within the limb 15 during the coagulation phase. For the cutting procedure, the cutting instrument 30 can be positioned on the already coagulated tissue and moved at a defined advance speed to cut through the tissue. This occurs in this embodiment example, for example, by a (non-depicted) control unit driving the cutting instrument 30, which unit can be activated by a finger switch 32. Since the cutting instrument 30 is configured as integrated in the electrosurgical instrument 10, a change of instrument and, with that, any interruption to the course of the operation can be avoided.

Alternatively, it is possible for the user to actuate the cutting instrument mechanically. The surgeon may then slide the blade 31, if required, through the limb 15 up to and through the tissue.

If no device is provided on the electrosurgical instrument for cutting the tissue, the guide opening should be constructed in such a way that an externally entering cutting instrument, e.g. surgical scissors, can be applied to the pretensioned tissue with sufficiently accurate guidance.

In the practical application, a spacer (not depicted) or similar device maintaining a clearance between the electrode parts 22, 23 is configured on the electrosurgical instrument 10, to avoid direct contact of the coagulating surfaces 22a, 23a of the electrode parts 22, 23 and, with that, a short circuit. The spacer may be configured, for example, on one of the limbs 15, 16.

Alternatively, it is possible to provide the spacer as an insulating section on the electrode parts. Because of heat-conducting properties of the insulating section, coagulation of the tissue is guaranteed on the latter too.

The electrosurgical instrument 10 depicted in FIG. 1 is, as already referred to above, configured for use on the opened body. The principle of the electrode parts configured with the clamping regions is also applicable to endoscopy. The electrode parts attached to the limbs and, if so required, the cutting instrument are then actuated via a hand grip attached to a shaft, for example, or a control unit may be provided, allowing actuation of the electrode parts and/or the cutting instrument to be controlled by this means.

Figure 2:
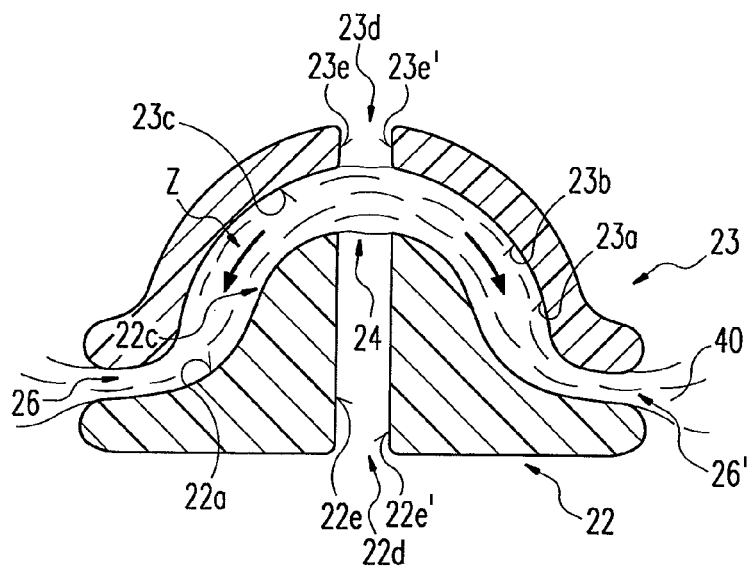
FIG. 2 is a schematic cross-sectional view of an electrode arrangement viewed from the front according to a second embodiment of electrosurgical instrument.
Figure 3:
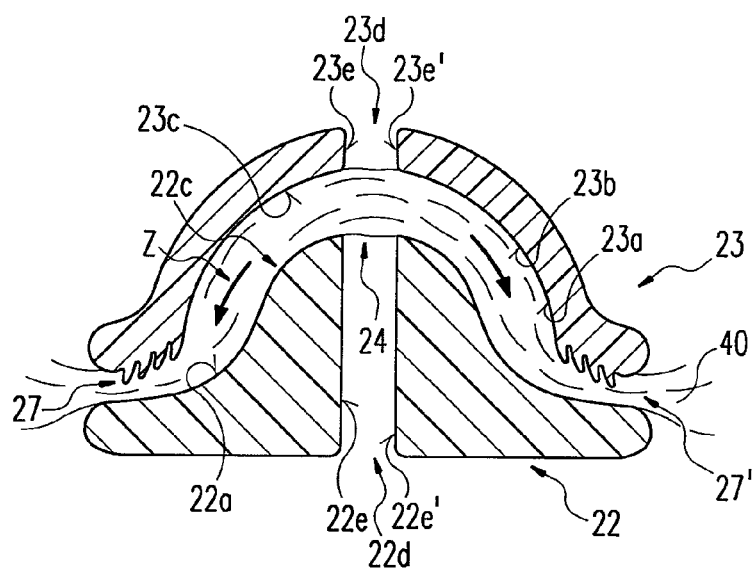
FIG. 3 is a schematic, cross-sectional view of an electrode arrangement viewed from the front according to a third embodiment of electrosurgical instrument.

FIGS. 2 and 3 each depict a considerably enlarged front elevation of an electrode arrangement as a cross-section in a second and third embodiment respectively. The electrode parts 22, 23 correspond essentially to the embodiment of those depicted in FIG. 1. These also have passages 22d, 23d serving as a guide opening 24 for a cutting instrument as described in FIG. 1. A surface profile supporting a clamping effect of clamped tissue 40 is configured on at least one clamping region. The profile is preferably configured at both end areas of the respective clamping region or the respective clamping regions 22c, 23c and additionally moves the tissue 40 in a direction of traction Z defined by the clamping regions 22c, 23c or prevents any retreating of the tissue 40 against this direction of traction Z.

As depicted in FIG. 2, coagulating surfaces 22a, 23a of the electrode parts 22, 23 are formed at their two end areas in such a way that the tissue 40 is taken along in the direction of the end areas when the limbs 15, 16 are brought together and, in each case when the limbs 15, 16 are brought together, is clamped in a constriction 26, 26' relative to the rest of the area. The constriction 26, 26' has also the advantage that the coagulating surfaces 22a, 23a can be configured essentially smooth and are thus easy to clean. In addition, damage to the tissue is prevented due to the smooth surface.

In FIG. 3 the electrode part 23 configured with a concave curvature 23b has a tooth-type profile 27, 27' at end areas. The teeth may be arranged in such a way, for example, that they reach further and further into the tissue 40 when the limbs are brought together and take this along in the direction of traction Z. As a result, the tension in the tissue 40 is significantly increased. It is essential, however, that damage to the tissue 40 is avoided by the profile 27, 27', with the result that the teeth are preferably configured as rounded nodules.

Preferably the nodules are arranged in such a way that the tissue 40 is held by the profile 27, 27' in its clamped position when the limbs are slightly opened. The profile 27, 27' accordingly functions as an arrangement of barbs.

Figure 4:
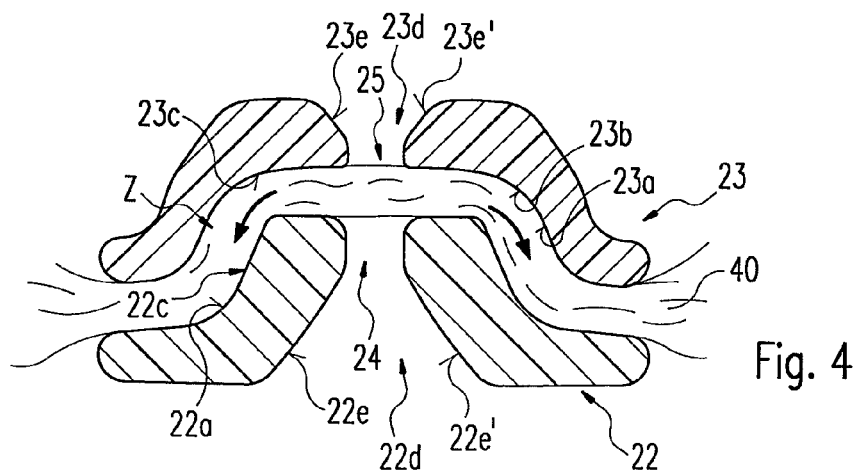
FIG. 4 is a schematic, cross-sectional view of an electrode arrangement viewed from the front according to a fourth embodiment of electrosurgical instrument.

FIG. 4 depicts an enlarged front elevation of an electrode arrangement as a cross-section in a fourth embodiment. In this case, passages 22d, 23d divide the respective electrode parts 22, 23 into at least two areas in such a way that the electrode parts 22, 23 each have opposing split surfaces 22e, 22e' and 23e, 23e' arranged in a tapering manner relative to each other in the direction of the coagulating surfaces 22a, 23a. Since the split surfaces 22e, 22e', 23e, 23e' of the corresponding electrode parts 22, 23 converge on one cutting area 25, this further guarantees precise guidance of the cutting instrument 30 here. The part of the passages 22d, 23d directed away from the cutting area 25 is particularly suited to reprocessing, that is to a cleaning of the instrument 10 after a successful intervention or also to the subsequent application of a coating of the split surfaces 22e, 22e', 23e, 23e' with, for example, a wear-resistant layer of ceramic, since improved accessibility is guaranteed due to the physical form of the passages 22d, 23d.

Figure 5:
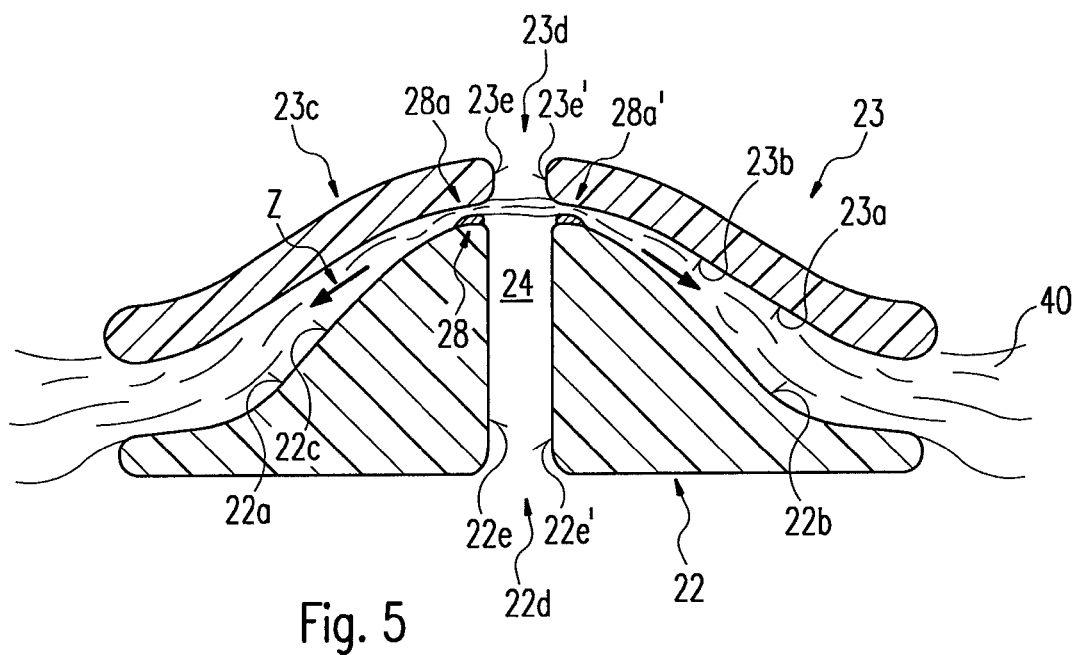
FIG. 5 is a schematic, cross-sectional view of an electrode arrangement viewed from the front according to a fifth embodiment of electrosurgical instrument.

FIG. 5 depicts an enlarged front elevation of an electrode arrangement as a cross-section in a fifth embodiment. This embodiment corresponds essentially to the one depicted in FIGS. 1 and 2. The difference is that clamping regions 22c, 23c are configured here with different radii of curvature; the radius of curvature of the concavely configured clamping region 23c is larger than the radius of curvature of the convexly configured one. As a result, the respective coagulating surfaces 22a, 23a are also correspondingly curved. The curvatures 22b, 23b run around longitudinal axes of the distal ends in such a way that tissue 40 held between the distal ends 11, 12 and running perpendicular to the longitudinal axes is held with increasing compression relative to central sections of the clamping regions 22c, 23c. Advantageously, tissue 40 once clamped here is arrested particularly securely between the clamping regions 22c, 23c due to the increasing compression. Any sliding of the tissue 40, once grasped, from out of the electrode parts 22, 23 is thus ruled out. In addition, safe closure of the tissue 40 is achieved at the areas of high compression, i.e. high pressure, due to the strong clamping force.

Directly adjacent to one passage 22d, a protruding insulating section 28 configured from two segments 28a, 28a' is provided on the convexly configured clamping region 22c, which is divided by the passage 22d into two areas. Preferably, the segments 28a, 28a' of the insulating section 28 run over the electrode part 22 parallel to a crown line of the clamping region 22c. This prevents a short circuit between the electrode parts 22, 23 when the same are brought together. The segments 28a, 28a' of the insulating section 28, on the one hand, support the clamping effect of the clamping region 22 and, on the other, enable the clamped tissue 40 to be bent. As a result, its reliable arresting between the electrode parts 22, 23 is guaranteed.

In principle, the insulating section is provided, depending on the physical form of the electrode parts, on areas of at least one clamping region or coagulating surface which are closest to the opposing coagulating surface. This is particularly necessary when the clamping regions and thus the coagulating surfaces have a different radius of curvature. Preferably, the insulating section is then arranged in a central area of the clamping region or clamping regions and thus prevents a short circuit between the electrode parts.

If the insulating section is configured on the areas of at least one coagulating surface in closest proximity to the opposing coagulating surface, it may close flush with the respective coagulating surface. To do this, however, it is necessary that a surface portion of the coagulating surface that describes the area in closest proximity to the opposing coagulating surface is configured completely from insulating material. Only in this way may contact between the conductive areas of the coagulating surfaces be avoided. With the convexly or concavely configured clamping regions with different radii of curvature, the insulating section should be arranged along a crown line of at least one clamping region, between the coagulating surfaces. In this embodiment, the insulating section is accommodated in a protected manner in the respective electrode part, counteracting any wear of the insulating section.

Figure 6:
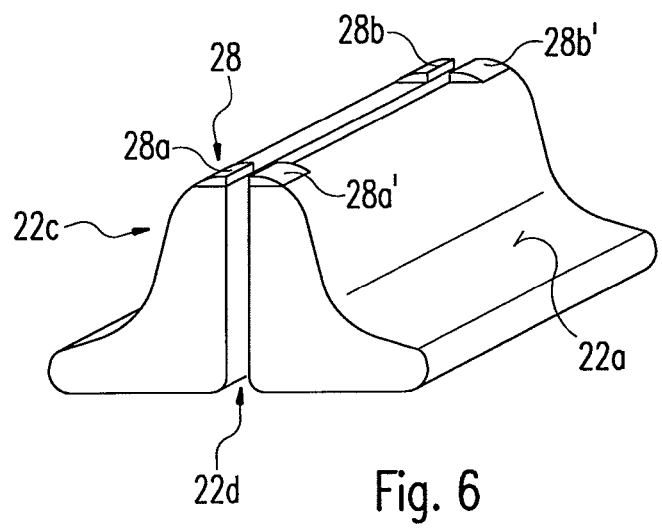
FIG. 6 is a perspective view of a clamping region of an electrode arrangement in the first embodiment shown in FIG. 1.

FIG. 6 depicts a perspective view of a convexly configured clamping region 22c according to FIG. 1. Here, an insulating section 28 is provided which consists of four segments 28a, 28a', 28a, 28a', wherein two segments are configured in each case at the respective areas of the clamping region 22c or the electrode part 22. The tissue being treated may be reliably arrested by means of several segments 28a, 28a', 28a, 28a' because it can be bent over edges of the segments 28a, 28a', 28a, 28a' of the insulating section 28. In addition, the coagulating surface 22a is only covered at few areas by the insulating section 28.

Alternatively, it is possible to configure the insulating section in a structured manner to further improve the arresting of the tissue.

Preferably, the insulating section is configured from ceramic or diamond, since both materials have, among other things, a high degree of resistance to corrosion and a high degree of resistance to wear from mechanical strain.

Advantageously, the insulating section may be configured as a surface profile supporting a clamping effect of the clamping regions. As a result, both the short circuit between the electrode parts is avoided and the tensioning of the tissue is reinforced in the simplest way.

LIST OF REFERENCE NUMERALS

10 Electrosurgical instrument
11 Distal end
12 Distal end
13 Proximal end
14 Proximal end
15 Limb
16 Limb
17 Spindle
18 Gripping part
19 Gripping part
20 Current connection element, current-supply device
21 Current connection element, current-supply device
22 Electrode part
22a Coagulating surface
22b Convex curvature
22c Clamping region
22d Passage
22e, 22e' Split surface
23 Electrode part
23a Coagulating surface
23b Concave curvature
23c Clamping region
23d Passage
23e, 23e' Split surface
24 Guide opening
25 Cutting area
26, 26° Constriction
27, 27' Profile
28 Insulating section
28a, 28a' Segment of the insulating section
28a, 28a' Segment of the insulating section
30 Cutting instrument
31 Blade
32 Finger switch
40 Tissue, vessel
Z Direction of traction

The invention claimed is:

1. An electrosurgical instrument including
two articulated limbs, which can be actuated in the manner of a cutting or clamping tool,
electrode parts with coagulating surfaces positioned opposite each other at distal ends of the limbs for gripping tissue and adapted to pass a coagulating current through said tissue to cause its coagulation,
current supply devices adapted to supply said coagulating current to said electrode parts from a HF generator, and
a cutting instrument,
wherein opposing clamping regions defined by said electrode parts are adapted to clamp said tissue whereby said tissue is pretensioned between said electrode parts and in order that a cutting procedure can be carried out on said pretensioned tissue by means of said cutting instrument,
wherein at least one of the clamping regions comprises a surface profile supporting a clamping effect, which is configured at two end areas of the respective clamping region, wherein the end areas are facing away from a center of the clamping regions, and additionally moves the tissue in a direction of traction away from the center of the clamping regions, the surface profile being configured as rounded nodules that function as an arrangement of barbs in such a way that the tension in the tissue caused by clamping the tissue between the opposing clamping regions remains in the tissue the when the limbs are slightly opened,
wherein passages are provided on the opposing clamping regions that divide the respective electrode parts into at least two areas, with the result that the electrode parts each have opposing, split surfaces, wherein the passages essentially adjoin each other in alignment when the limbs are brought together, and wherein one of said limbs is configured and adapted to accommodate said cutting instrument at a position within a passage of said one limb, and said cutting instrument is moveable between said position within the passage of said one limb and positions at which said cutting instrument cuts through said pretensioned vessel or tissue.

2. The electrosurgical instrument according to claim 1, wherein one of said clamping regions is curved in a convex manner at least in a first central section and another opposing clamping region is curved in a concave manner at least in a second central section such that, when said limbs are brought together, these clamping regions fit together.

3. The electrosurgical instrument according to claim 1, wherein one of said clamping regions is curved in a convex manner at least in a first central section and another opposing clamping region is curved in a concave manner at least in a second central section, a radius of curvature of said concavely curved clamping region being larger at least in the second central section than a radius of curvature of said convexly curved clamping region in the first central section, and wherein said curvatures run along longitudinal axes of said distal ends whereby tissue clamped between said distal ends and running perpendicular to said longitudinal axes is retained by a pressure that increases in directions towards said first and said second central sections.

4. The electrosurgical instrument according to claim 1, wherein said opposing, split surfaces are arranged parallel to each other.

5. The electrosurgical instrument according to claim 1, wherein each of said opposing, split surfaces taper in the direction of the coagulating surfaces.

6. The electrosurgical instrument according to claim 1, wherein said passages provided on the opposing clamping regions adjoin each other in alignment when the limbs are brought together.

7. The electrosurgical instrument according to claim 1 wherein said cutting instrument is connected to the electrosurgical instrument.

8. The electrosurgical instrument according to claim 1 wherein said cutting instrument is adapted to be actuated by at least one of a mechanical or an electrical means.

9. The electrosurgical instrument according to claim 1, wherein said surface profile is configured as a saw-tooth profile.

10. The electrosurgical instrument according to claim 1, wherein said surface profile is configured such that at least one constriction is provided between the electrode parts.

11. The electrosurgical instrument according to claim 1 wherein an insulating section is provided on at least one of the coagulating surfaces that prevents direct electrical contact between the coagulating surfaces.

12. The electrosurgical instrument according to claim 11, wherein said insulating section is made up from several segments.

13. The electrosurgical instrument according to claim 11, wherein said insulating section is structurally formed.

14. The electrosurgical instrument according to claim 11 wherein said insulating section is constructed from ceramic or from diamond.

15. The electrosurgical instrument according to claim 11 wherein said insulating section is configured as a surface profile that aids said clamping effect.

16. The electrosurgical instrument according to claim 1 wherein said instrument is configured as a laparoscopic instrument.

* * * * *